United States Patent [19]

Suzuki

[11] Patent Number: Plant 7,341

[45] Date of Patent: Oct. 2, 1990

[54] ROSE PLANT — KEIJOURNA VARIETY

[75] Inventor: Seizo Suzuki, Tokyo, Japan

[73] Assignee: The Conard-Pyle Company, West Grove, Pa.

[21] Appl. No.: 365,823

[22] Filed: Jun. 14, 1989

[51] Int. Cl.[5] ..... A01H 5/00

[52] U.S. Cl. ..... Plt./21

[58] Field of Search ..... Plt./20, 21

*Primary Examiner*—James R. Feyrer

*Attorney, Agent, or Firm*—Burns, Doane, Swecker & Mathis

[57] ABSTRACT

A new and distinct variety of Hybrid Tea rose plant is provided which forms in abundance attractive very large double blossoms of long vase life. The blossoms are vermilion red on the upper surface and cardinal red on the under surface. The plant exhibits an erect growth habit, forms vigorous vegetation and is well suited for cut flower production. Good resistance to diseases is manifest.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was an unnamed seedling. The male parent (i.e., the pollen parent) of the new variety was the Meirodium variety (U.S. Plant Pat. No. 4,037). The parentage of the new variety can be summarized as follows:

Unnamed Seedling × Meidrodium.

The seeds resulting from the above pollination were sown and plantlets were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive very large double blossoms which are vermilion red on the upper surface and cardinal red on the under surface and exhibit a long vase life,
(b) exhibits an erect growth habit,
(c) is well suited for cut flower production in a greenhouse,
(d) forms vigorous vegetation, and
(e) exhibits good resistance to cryptogamic diseases.

The blossom production of plants of the new variety is high particularly when the stem length is considered.

The new variety well meets the needs of the horticultural and is particularly well-suited for the production of cut flowers.

The new variety has been found to undergo asexual propagation by a number of routes, including budding, grafting, cuttage, etc. The characteristics of the new variety have been found to be strictly transmissible by such asexual propagation from one generation to another.

The new variety has been named the Keijourna variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and observed during February while grafted on *Rosa indicia* understock and growing in greenhouse at Cap d'Antibes, France.

FIG. 7 illustrates a specimen of an open flower — plan view — reverse;

DETAILED DESCRIPTION

Figures 1, 2, 3, 4, 5, 6, 8, 9, 10, 11, 12, 13, 14, 15, 16:
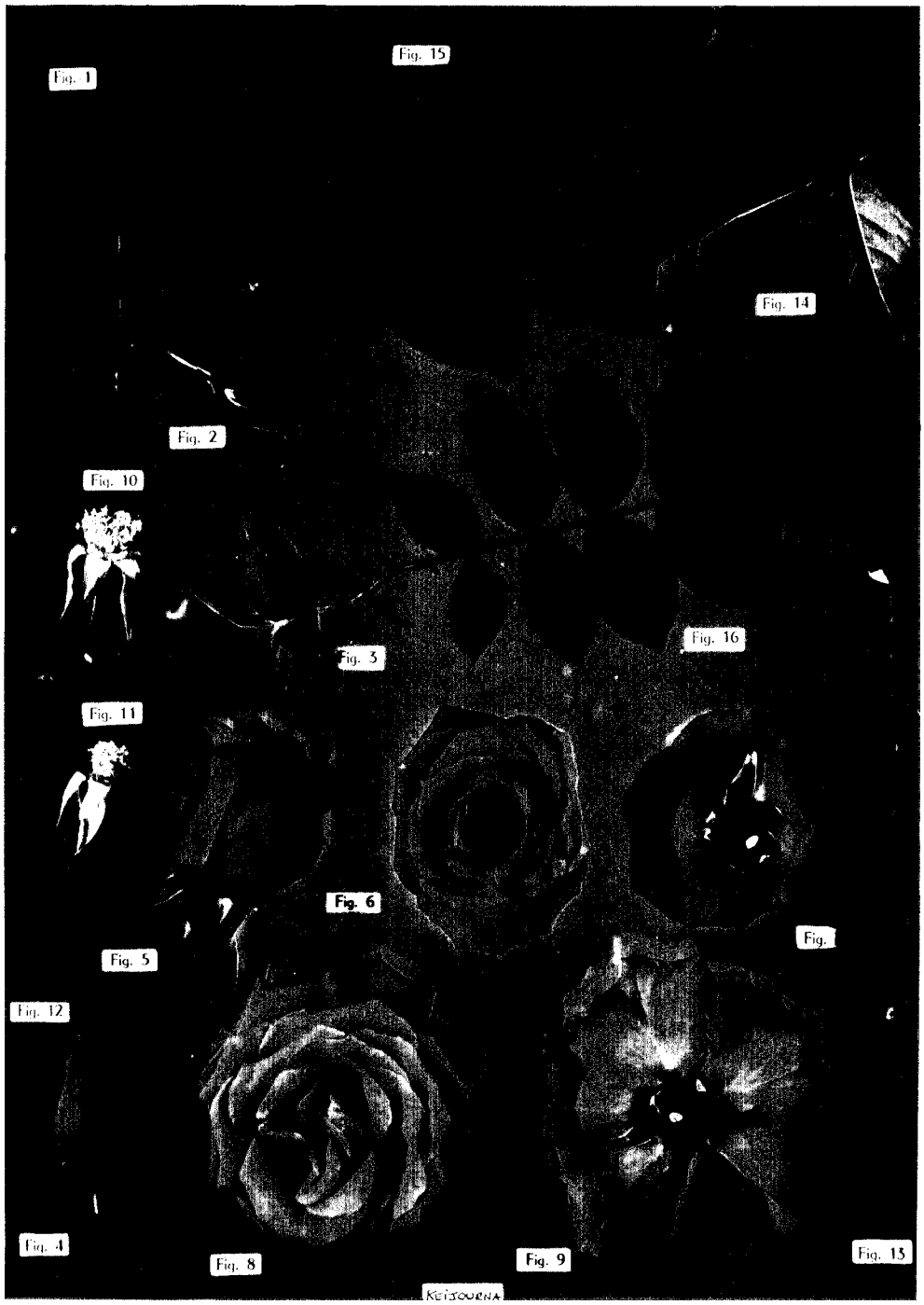
FIG. 1 illustrates a specimen of a young shoot.
FIG. 2 illustrates a specimen of a floral bud before the opening of the sepals.
FIG. 3 illustrates a specimen of a floral bud as the sepals open.
FIG. 4 illustrates a specimen of a floral bud when the petals open.
FIG. 5 illustrates a specimen of a flower in the course of opening.
FIG. 6 illustrates a specimen of an open flower — plan view — obverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — under surface.
FIG. 15 illustrates a specimen of a leaf with five leaflets — plan view — upper surface.
FIG. 16 illustrates a specimen of a leaf with nine leaflets — plan view — upper surface.

The chart used in the identification of the colors is that of The Royal Horticultural Society (R.H.S. Colour Chart). The description is based on observations of one year old specimens made during February while grafted on *Rosa indica* understock and growing in greenhouses at Cap d'Antibes, France. Color terminology in common terms precedes the reference to such chart.

Class: Hybrid Tea.

Plant:

*Height.*—Plants which were pruned to a height of 85 cm. commonly produced floral stems having a length of approximately 50 to 90 cm.

*Habit.*—Erect.

Branches:

*Color.*—Young stems: light green, Green Group 137B, more or less stained with reddish coloration. Adult wood: medium green, Yellow-Green Group 146B.

*Thorns.*—Size: Medium. Quantity: few. Color: reddish on young stems and pinkish changing to tan on mature wood.

Leaves:

*Stipules.*—Adnate, pectinate, wide and jagged.

*Petioles.*—Upper surface: striped reddish brown on young foliage and medium green on adult foliage with more or less glandular edges. Under surface: light green, bear some small hooked prickles.

*Leaflets.*—Number: 3, 5, 7 (most often), and 9. Shape: spear-shaped. Serration: single and regular. Texture: consistent. General appearance: bright, full and dense foliage. Color (young foliage): Upper surface: medium green, Green Group 137A, more or less stained with reddish coloration. Under surface: light green, Green Group 138B. Color (adult foliage): Upper surface: dark green, Green Group 137A. Under surface: light green, Green Group 137C.

Inflorescence:

*Number of flowers.*—General one per stem.

*Peduncle.*—Straight, upright, slightly stained with reddish coloration, bear numerous reddish prickles, approximately 15 to 18 cm. in length on average.

*Sepals.*—Upper surface: tomentose, and greenish in coloration. Under surface: medium green in coloration, more or less stained with reddish brown, the outside sepals have edges which are appendiculated and often end in a well-developed leaf-like appendix.

*Buds.*—Shape: conical and elongated. Length: approximately 5 to 6 cm. on average. Size: very large. Color upon opening: Upper surface: strawberry red, Red Group 46B, and darker at the edge of the petals. Under surface: currant red, Red Group 46A.

*Flower.*—Shape: elongated, high centered when opening changing to cuplike when fully open. Diameter: approximately 13 to 14 cm. on average. Color (when open begins): Upper surface: guardsman red, Red Group 45A. Under surface: currant red, Red Group 46A. Color (when blooming): Upper surface: vermilion red, Red Group 44A. Under surface: cardinal red, Red Group 53C. Color (at end of opening): Upper surface: vermilion red, Red Group 44A. Under surface: cardinal red, Red Group 53C. Fragrance: slight. Lasting Quality: long. Petal number: approximately 31 to 33 on average plus 2 or 3 petaloids commonly are present. Petal form: generally rounded. Texture: consistent. Petal drop: good. Stamen number: Approximately 256 to 259 on average commonly are observed. Anthers: normal, pale yellow in coloration. Filaments: dark fuschia with yellow base, or irregular heights. Pistils: approximately 206 to 266 on average commonly are observed. Stigmas: strawlike, sometimes bonded together, located above the stamens. Styles: light fuschia, tomentose at the base, more or less twisted, of irregular heights. Receptacle: smooth, light green in coloration, and in longitudinal section in the shape of a pitcher.

Development:

*Vegetation.*—Vigorous.

*Blooming.*—Very floriferous.

*Aptitude to forcing.*—Fair.

*Resistance to diseases.*—Good.

I claim:

1. A new and distinct variety of Hybrid Tea rose plant characterized by the following combination of characteristics:

(a) forms in abundance attractive very large double blossoms which are vermilion red on the upper surface and cardinal red on the under surface and exhibit a long vase life, (b) exhibits an erect growth habit, (c) is well suited for cut flower production in a greenhouse, (d) form vigorous vegetation, and (e) exhibits good resistance to cryptogamic diseases;

substantially as herein shown and described.

* * * * *

Fig.

KEISOURNA